United States Patent
Pomerantz et al.

(10) Patent No.: US 9,335,280 B2
(45) Date of Patent: May 10, 2016

(54) MOBILE TRANSPORT AND SHIELDING APPARATUS FOR REMOVABLE X-RAY ANALYZER

(71) Applicant: X-RAY OPTICAL SYSTEMS, INC., East Greenbush, NY (US)

(72) Inventors: Steven M. Pomerantz, Ashland, MA (US); John H. Burdett, Charlton, NY (US); Rory D. Delaney, Slingerlands, NY (US)

(73) Assignee: X-RAY OPTICAL SYSTEMS, INC., East Greenbush, NY (US)

( * ) Notice: Subject to any disclaimer, the term of this patent is extended or adjusted under 35 U.S.C. 154(b) by 39 days.

(21) Appl. No.: 14/349,732

(22) PCT Filed: Oct. 3, 2012

(86) PCT No.: PCT/US2012/058576
§ 371 (c)(1),
(2) Date: Apr. 4, 2014

(87) PCT Pub. No.: WO2013/052556
PCT Pub. Date: Apr. 11, 2013

(65) Prior Publication Data
US 2014/0328468 A1    Nov. 6, 2014

Related U.S. Application Data

(60) Provisional application No. 61/544,069, filed on Oct. 6, 2011.

(51) Int. Cl.
*H05G 1/02*    (2006.01)
*G01N 23/10*   (2006.01)
*G01N 23/223*  (2006.01)

(52) U.S. Cl.
CPC .............. *G01N 23/10* (2013.01); *G01N 23/223* (2013.01); *G01N 2223/076* (2013.01);
(Continued)

(58) Field of Classification Search
CPC ... G01N 23/223; G01N 23/10; G01N 23/222; G21K 2201/062; G21K 2201/064
USPC ................................. 378/195, 204
See application file for complete search history.

(56) References Cited

U.S. PATENT DOCUMENTS 5,175,755 A    12/1992    Kumakhov et al.
5,192,869 A    3/1993     Kumakhov et al.
(Continued)

FOREIGN PATENT DOCUMENTS

| EP | 1744151 A1 | 1/2007 |
| JP | 2003156458 A | 5/2003 |
| WO | WO-2009111454 A1 | 9/2009 |

OTHER PUBLICATIONS

International Search Report for PCT/US2012/058576 dated Mar. 28, 2013.

*Primary Examiner* — Courtney Thomas
(74) *Attorney, Agent, or Firm* — Jeffrey Klembczyk, Esq.; Kevin P. Radigan, Esq.; Heslin Rothenberg Farley & Mesiti P.C.

(57) ABSTRACT

A mobile transport and shielding apparatus, which holds an x-ray analyzer for transport between operating sites, and also serves as a shielded, operational station for holding the x-ray analyzer during operation thereof. The x-ray analyzer is removably insertable into the apparatus and is operable either within the mobile transport and shielding apparatus, or outside of the apparatus. The apparatus may provide means to control, power, cool, and/or charge the x-ray analyzer during operation of the analyzer; and also means to transport the analyzer (e.g., a handle).

13 Claims, 10 Drawing Sheets

(52) U.S. Cl.
CPC ... *G01N 2223/301* (2013.01); *G01N 2223/308* (2013.01); *G01N 2223/309* (2013.01); *G21K 2201/062* (2013.01); *G21K 2201/064* (2013.01)

(56) References Cited

U.S. PATENT DOCUMENTS

| | | |
|---|---|---|
| 5,497,008 A | 3/1996 | Kumakhov et al. |
| 5,570,408 A | 10/1996 | Gibson et al. |
| 5,604,353 A | 2/1997 | Gibson et al. |
| 5,745,547 A | 4/1998 | Xiao et al. |
| 6,285,506 B1 | 9/2001 | Chen et al. |
| 6,317,483 B1 | 11/2001 | Chen et al. |
| 6,934,359 B2 | 8/2005 | Chen et al. |
| 7,035,374 B2 | 4/2006 | Chen et al. |
| 7,072,439 B2 | 7/2006 | Radley et al. |
| 7,110,506 B2 | 9/2006 | Radley et al. |
| 7,209,545 B2 | 4/2007 | Radley et al. |
| 7,738,629 B2 | 6/2010 | Chen et al. |
| 2005/0226373 A1 | 10/2005 | Trombka et al. |
| 2009/0225948 A1 | 9/2009 | Burdett, Jr. et al. |
| 2009/0274274 A1 | 11/2009 | He et al. |
| 2010/0278312 A1* | 11/2010 | Ortiz .................. 378/195 |
| 2011/0170666 A1 | 7/2011 | Chen et al. |

* cited by examiner

# MOBILE TRANSPORT AND SHIELDING APPARATUS FOR REMOVABLE X-RAY ANALYZER

CROSS-REFERENCE TO RELATED APPLICATION

This application is a continuation of PCT Application PCT/US2012/058576, filed Oct. 3, 2012 and published under the PCT Articles in English as WO 2013/052556 A2 on Apr. 11, 2013. PCT Application PCT/US2012/058576 also claims the benefit of U.S. provisional patent application Ser. No. 61/544,069, filed Oct. 6, 2011, each of which is hereby incorporated herein by reference in its entirety.

TECHNICAL FIELD

The present invention relates to a transport apparatus for a removable x-ray analyzer, to present a sample accurately to the x-ray analyzer where minimization of x-ray leakage and precise sample positioning are required, and also to provide protected transport of the analyzer.

BACKGROUND OF THE INVENTION

X-ray analysis of samples is a growing area of interest across many industries such as medical, pharmaceutical, and petroleum. Moving analysis from the laboratory to the field is becoming increasing popular for many reasons, including reduction in size and costs of analyzer components, as well as industry's continually increasing needs for better and faster data collection in areas remote from a laboratory (e.g., production lines, store shelves, raw material sites, mobile compliance vans, transportation and customs hubs, etc.). Moving sensitive instruments to these areas presents certain challenges, including shielding, sample presentation, vibration damping, etc. for which unique resolutions are in continuing demand.

For example, sample handling is of critical importance in such systems, as is x-ray shielding. It is a general requirement of x-ray analysis systems to minimize x-ray exposure during sample analysis, and also during loading and unloading. During sample loading, this can accomplished by interlock systems which mechanically and/or electrically control an x-ray blocking "shutter" mechanism over the x-ray source and/or a relay to a high voltage power supply powering an x-ray tube. An interlock system senses an operator opening the system to load/unload a sample, and automatically activates the shutter (or relay) to completely stop any x-rays from transmitting through the now-open sample door, toward an operator. Shielding during sample measurement is also required, and can be provided by sample covers, enclosures, shields and the like, and/or by creating adequate distance between the user and the x-rays.

Moreover, any sample insertion and removal technique should also present the sample to the x-ray measurement engine at a controlled distance (e.g., along a z-axis) for proper alignment to the requisite x-ray analysis spot. This z-axis alignment is critically important for x-ray optic enabled analyzers (such as the MWD XRF and ME EDXRF x-ray engines discussed below) because of the sensitivity of the measurement to the focal areas of one or two separate optics in the x-ray excitation and/or detection paths. For example, U.S. Pat. Nos. 6,934,359 and 7,072,439, hereby incorporated by reference herein in their entirety and assigned to X-Ray Optical Systems, Inc., the assignee of the present invention, disclose monochromatic wavelength dispersive x-ray fluorescence (MWD XRF) techniques and systems for the analysis of samples. Monochromatic excitation, energy dispersive x-ray fluorescence (ME-EDXRF) analyzers are also gaining wide market acceptance, as disclosed in, e.g., commonly assigned US Publication 2011-0170666A1 entitled XRF System Having Multiple Excitation Energy Bands In Highly Aligned Package, the entirety of which is hereby incorporated by reference herein.

Handheld x-ray analyzer configurations, which have been broadly marketed in the recent past, meet certain performance and regulatory criteria. However, certain jurisdictions are particularly strict on the "open beam" nature of handheld instruments; and certain practical constraints (i.e., long measurement times, high power usage, limited resolution) may limit their use in certain applications.

What is required, therefore, is a transport apparatus for an x-ray analyzer, which minimizes x-ray leakage during sample loading and measurement, provides precise alignment of a sample to an x-ray analyzer focal area, and provides more convenient, reliable, and protective transport for sensitive x-ray analysis equipment.

SUMMARY OF THE INVENTION

The shortcomings of the prior art are overcome and additional advantages are provided by the present invention which in one aspect is a mobile transport and shielding apparatus, which holds an x-ray analyzer for transport between operating sites, and also serves as a shielded, operational station for holding the x-ray analyzer during operation thereof. The x-ray analyzer is removably insertable into the apparatus and is operable either within the mobile transport and shielding apparatus, or outside of the apparatus. The apparatus may provide means to control, power, cool, and/or charge the x-ray analyzer during operation of the analyzer; and also means to transport the analyzer (e.g., a handle).

Further additional features and advantages are realized through the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in connection with the accompanying drawings in which:

DETAILED DESCRIPTION OF THE INVENTION

Figure 1:
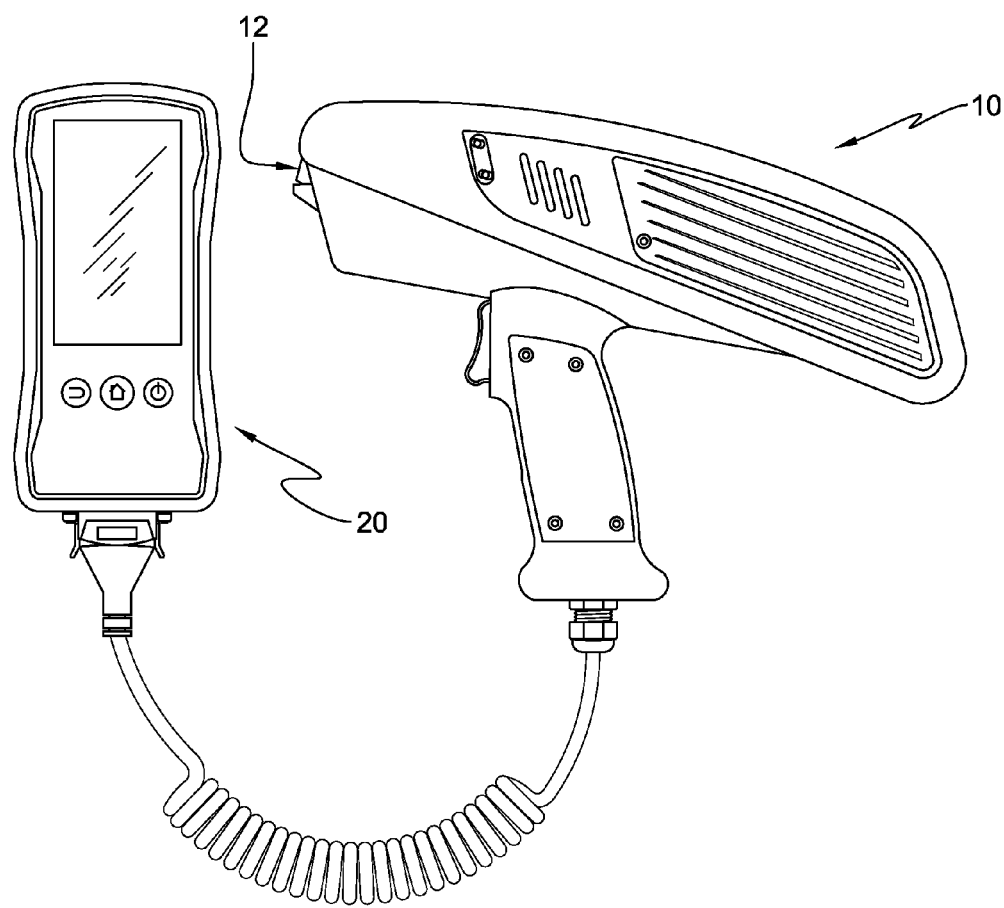
FIG. 1 is a perspective view of an exemplary handheld x-ray analysis instrument and related human interface module.

In accordance with the present invention, and with reference to FIG. 1, a handheld x-ray analyzer 10 typically includes an aperture 12 against which a sample is typically placed. Handheld x-ray analyzers have gained in popularity over the last few years because of their transportability and ease of use. However, the transport and use of these analyzers, as well as more advanced x-ray engines of the type discussed herein, in various operational environments presents challenges in the areas of shielding, sample handling and system transportation. Also shown in FIG. 1 is a human interface module 20, which may include the user interface and/or a power source for the handheld analyzer 10. Such an interface may also be integral to the analyzer 10.

Figure 2A:
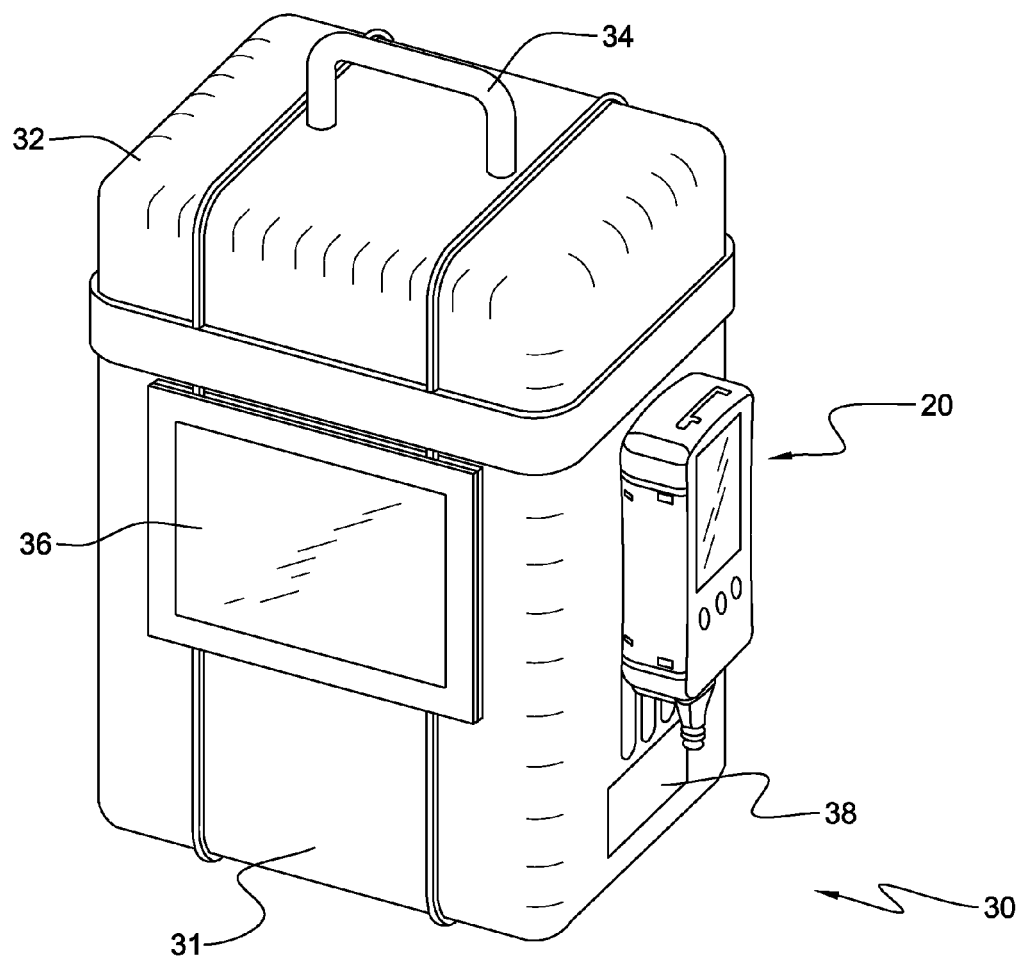
FIGS. 2a-c are perspective views of a mobile transport and shielding apparatus in accordance with the present invention, for an x-ray analyzer.
Figure 2B:
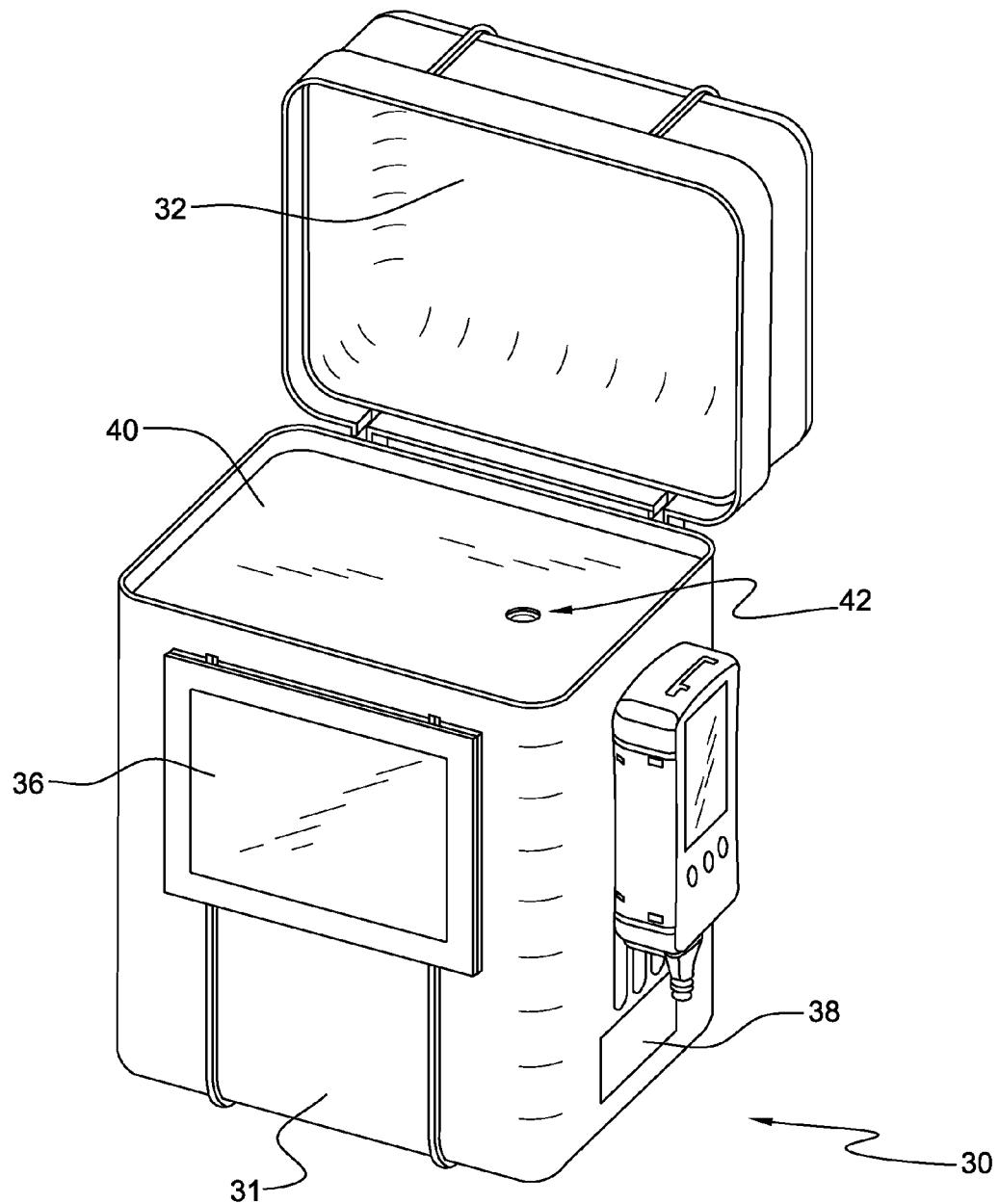
Figure 2C:
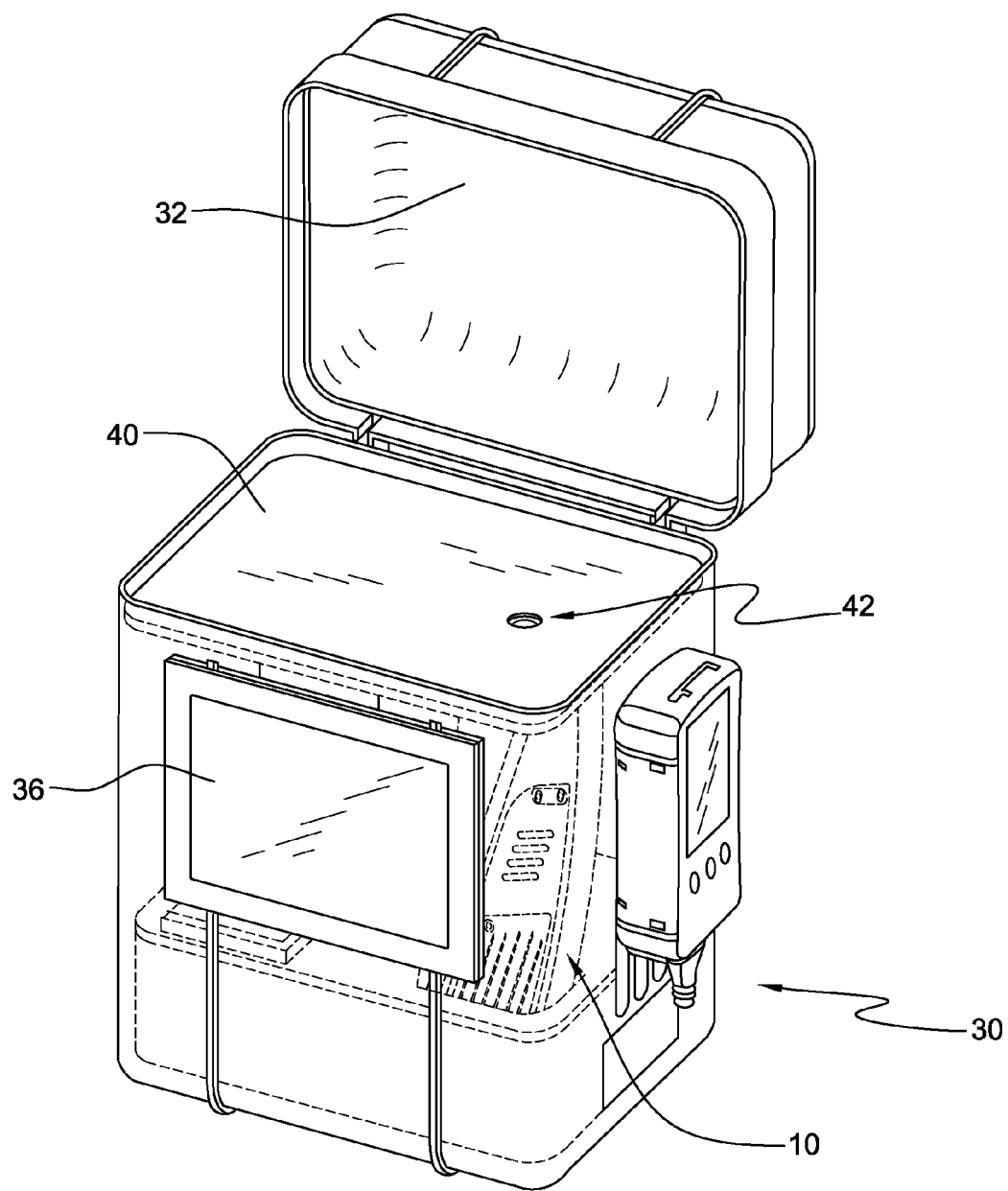

In accordance with the present invention, and with reference to the perspective views of FIGS. 2a-c (where like elements are designated with like numerals), an exemplary mobile transport and shielding apparatus 30 is disclosed for e.g., transporting, holding, shielding, and operating an x-ray analyzer. The example shown is in the form of an outer body having a lower portion 31, and an upper cover portion 32. These portions can be shielded to the extent necessary using integral materials such as aluminum, lead, or the like, to limit stray x-ray radiation during analyzer operation. The case may also include a handle 34 suitably sized for carrying the entire apparatus including the analyzer; an outer screen 36 (e.g., a touch screen for interfacing to/controlling the analyzer); and an interface port 38 for providing another interface to a removably mounted human interface module 20 (here mounted on the exterior of the case), and/or to provide ventilation to the interior of the case and therefore to the analyzer, and/or to carry AC power to the interior of the apparatus. Notably, FIG. 2a shows a closed unit, "closed beam" configuration which does not allow any x-ray radiation to escape the unit during operation.

With particular reference to FIGS. 2b-c (FIG. 2c is partially transparent to show the interior of the apparatus) where top portion 32 in a hinged open position, the handheld x-ray analyzer 10 may be removably mounted in the lower portion 31 and below a sample platform 40. Analyzer 10 is mounted such that sample aperture 42 of a (e.g., removable) sample stage 40 coincides with sample aperture 12 (shown above) of the analyzer. Sample stage 40 may also be formed of an x-ray shielding material.

In accordance with the present invention, x-ray analyzer 10 may be removably mounted in apparatus 30 such that it can function as a typical handheld analyzer outside of apparatus 30, or, in accordance with the present invention, can be quickly mounted in apparatus 30 which includes extra shielding (31, 32, 40); a stable sample stage 40 with sample aperture 42; mounting for interface module 20; and/or a larger screen 36 for field operation. In this capacity the transport apparatus 30 is adapted to hold, power, shield, and operate the analyzer; and to transport the analyzer when it is not operational.

Figure 3A:
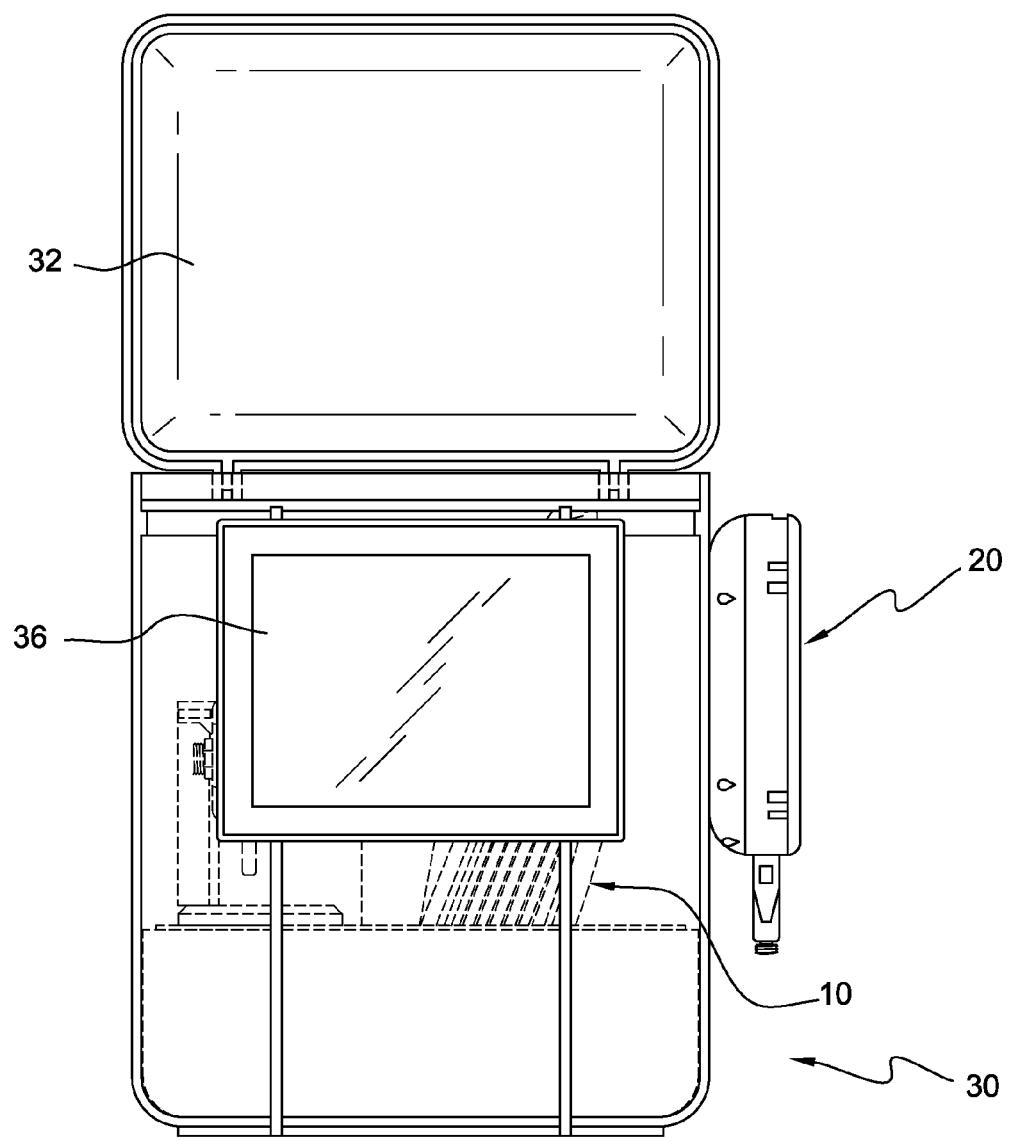
FIGS. 3a-b are front views of a mobile transport and shielding apparatus in accordance with the present invention.
Figure 3B:
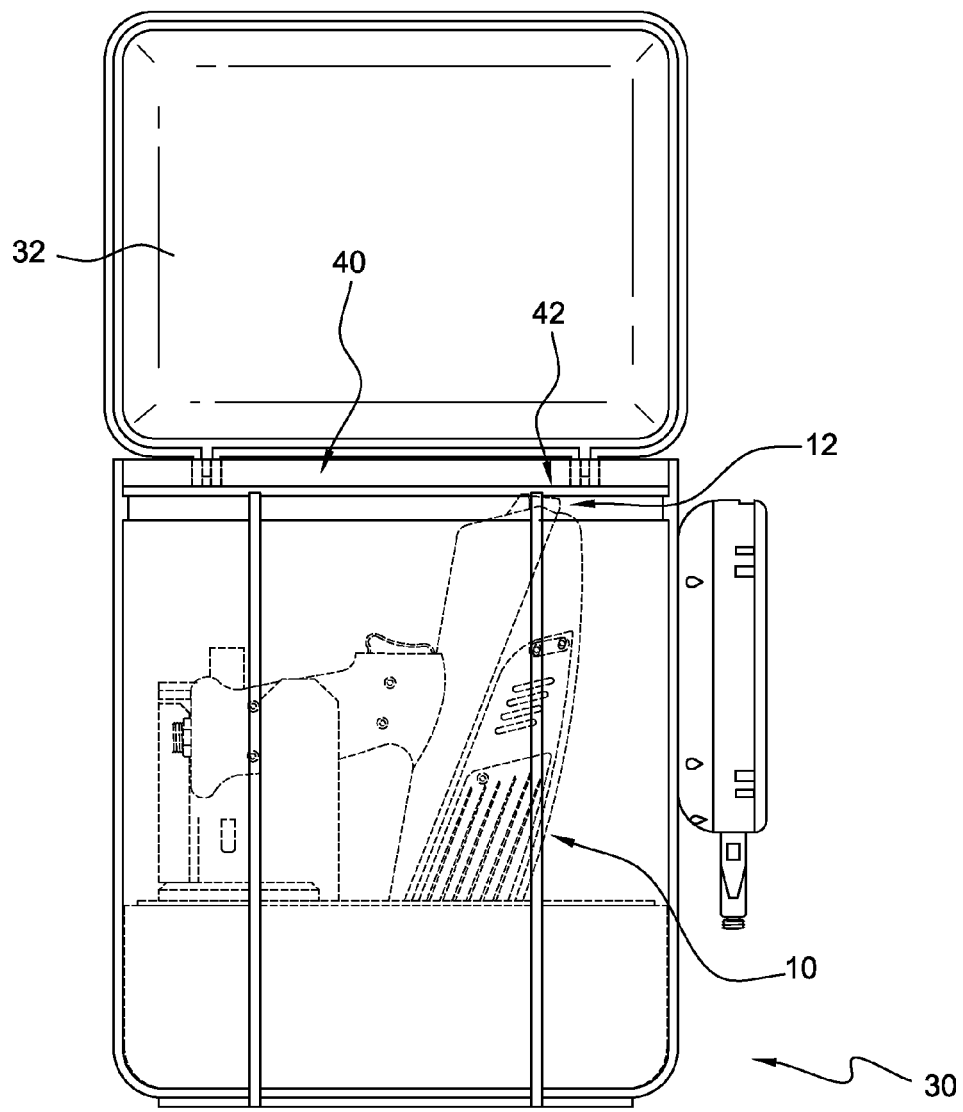

The front views of FIG. 3a (where like elements are designated using like reference numerals), shows a larger screen 36 mounted to the front of the apparatus for, e.g., interfacing to analyzer 10 when mounted in apparatus 30. FIG. 3b (where screen 36 is transparent to show interior detail) shows analyzer 10 in its mounted position, pointing upward such that its aperture 12 corresponds with the sample aperture 42 in sample stage 40.

Figure 4A:
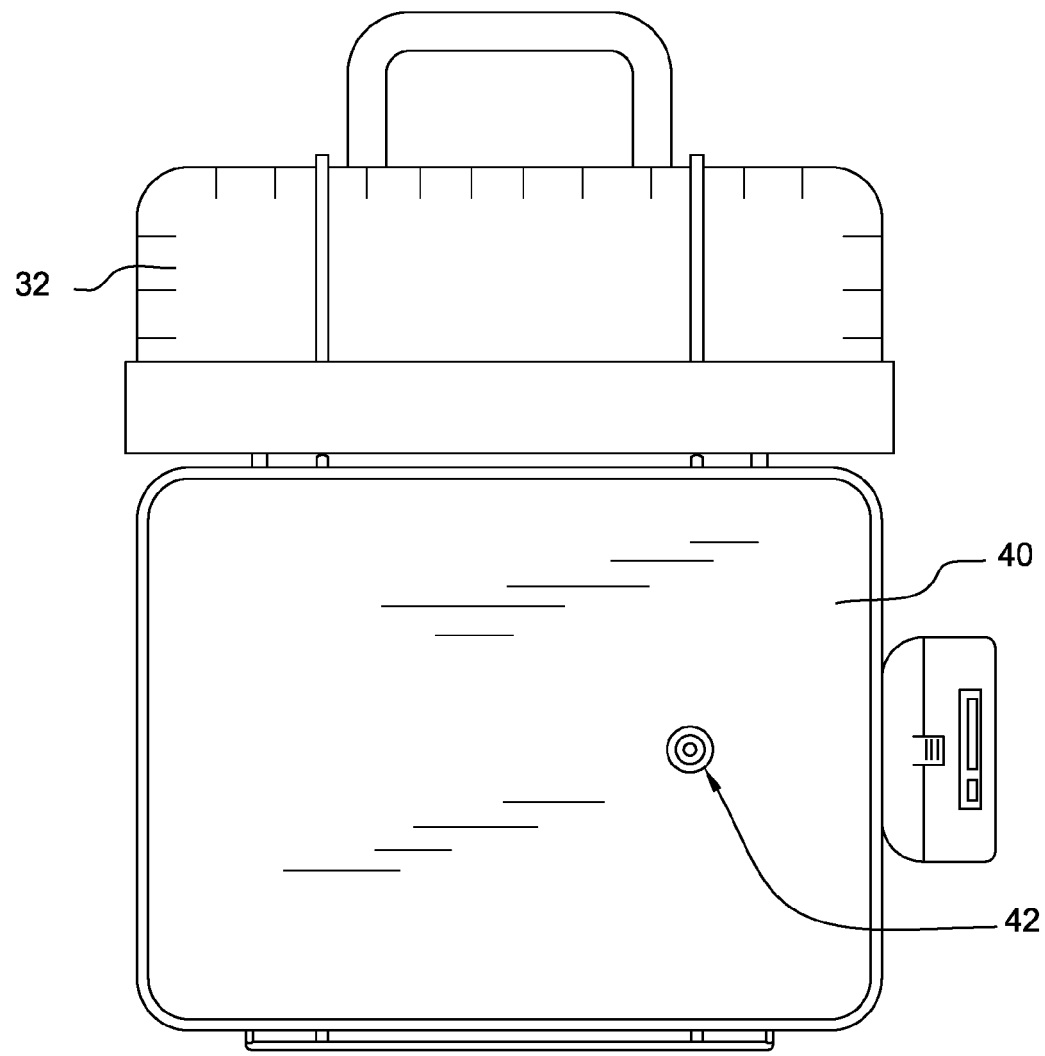
FIGS. 4a-b are top, open views of a mobile transport and shielding apparatus in accordance with the present invention.
Figure 4B:
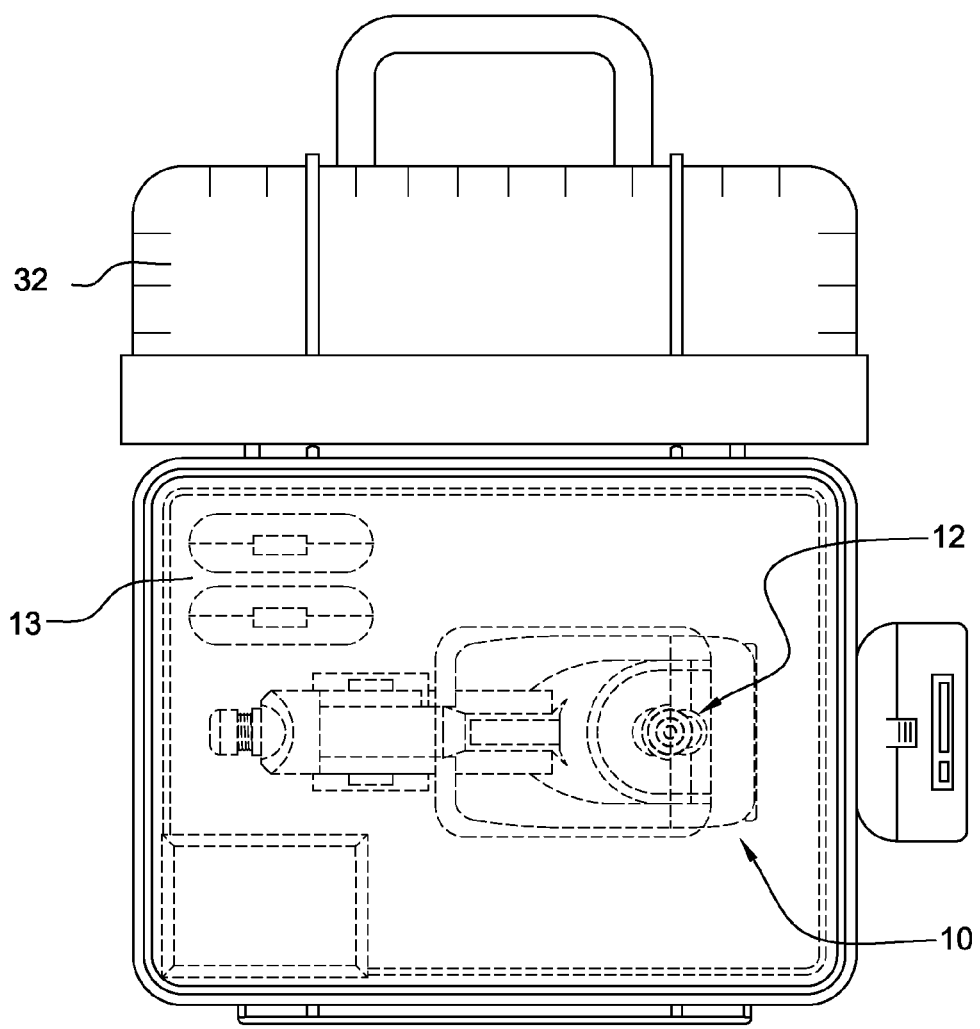

Similarly, the top views of FIG. 4a (where like elements are designated using like reference numerals), show sample stage 40 and aperture 42 from this view. FIG. 4b (where sample stage 40 is transparent to show interior detail) shows analyzer 10 in its mounted position, pointing upward such that its aperture 12 corresponds with the sample aperture 42 in sample stage 40. Also shown is exemplary, auxiliary storage for, e.g., spare batteries 13.

The present invention in one aspect is a transport apparatus (e.g., case) doubling as an operational station with integral sample stage. It ships as one unit, with the ability to easily change between typical handheld operation, and fixed mobile platform operation. Other features may include:

The outer body is preferably of rugged design, and dust- and water-proof. It accommodates an optional touch screen display (i.e., larger than the display of module 20).

The apparatus can also be adapted to be a charging station for the analyzer itself and/or spare batteries, using AC power provided to the apparatus from typical power grids e.g., 100-240 VAC 50-60 Hz.

The sample stage may be comparatively large and also may include accessible, plug in sampling accessories.

Integrated cooling may be provided using an air duct/plenum.

Upper radiation shield/cover is interlocked and radiation safe for closed beam operation.

Plug in connections may be provided for devices such as a printer, GPS, Bluetooth, data networks, wireless nodes, sample spinners, etc.

Target weight complete with analyzer and battery is >25 lbs, and approx 10"D, 15"W, 18"H outer dimensions.

A sample chamber (when the lid is closed) may include a stage size of 9×12 inches or greater—with cover height of at least 4.5 inches—with optional holes/indents for pin in place accessories/holders.

A camera can also be employed for sample positioning and documentation.

In one embodiment, two part construction may be provided including an inner docking station module for the analyzer, and an outer transport case. The inner docking station will slide out or easily be removed from case. In either embodiment, the handheld analyzer will easily & repeatably snap in and out of place.

The present invention also provides important safety features. In general, the apparatus will be stable (not tip over) with lid open or closed. The shielded cover can be interlocked, i.e., activated for x-ray measurement upon closing, and deactivated when opening. The interlock can work with a shutter over the x-ray beam and/or power to the x-ray source to ensure that no radiation is transmitted to the sample area when the cover is not in place.

In its full closed beam configuration, radiation safety of the system will comply with requirements as summarized by the "Suggested State Regulations for Control of Radiation" and other relevant documents which mandate radiation leakage to be at or below certain levels. In addition warning lights can be included as necessary which can be illuminated whenever the x-ray tube is energized.

Environmental factors are considered and addressed by the present invention, because factory temperatures can range from 5-40° C. (40-105° F.), and humidity may peak at 100%; and field & factory environments may contain high dust levels. Hence the enclosures, and enclosed cooling, provided by the present invention.

The handheld x-ray analyzers useable with the present invention include virtually any portable instruments amenable for movement into or out of the transport apparatus of the present invention, and which would benefit from the advantages provided by the present invention. The x-ray-optic-enabled engines discussed further below are of particular interest, and could benefit from the present invention, because of their need for reliable transportability (i.e., they are sensitive to alignment) and also because they perform optimally when the sample is highly aligned to the input and/or out focal areas of x-ray optics.

Other variations may include any particular orientation of the analyzer, body or cover, and also embodiments including moveable sample holders, e.g., into and out of the sample area.

For example, the doubly curved crystal (DCC) optics discussed further below direct an intense micron-sized monochromatic x-ray beam to the sample to enhance conventional XRF. These 3-D shaped optics selectively focus a very narrow band of x-ray wavelengths for sample excitation, according to Bragg diffraction laws.

Optics for advanced XRF systems, including those below, may include, for example, curved crystal monochromating optics such as those disclosed in commonly assigned U.S. Pat. Nos. 6,285,506; 6,317,483; and 7,035,374; and/or multilayer optics such as those disclosed in commonly assigned U.S. Patent Application entitled "X-Ray Focusing Optic Having Multiple Layers With Respective Crystal Orientations," U.S. Ser. No. 11/941,377 filed Nov. 16, 2007; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506 and 7,209,545 are also useable. Each of the above-noted patents and patent applications is incorporated herein by reference in its entirety.

Figure 5:
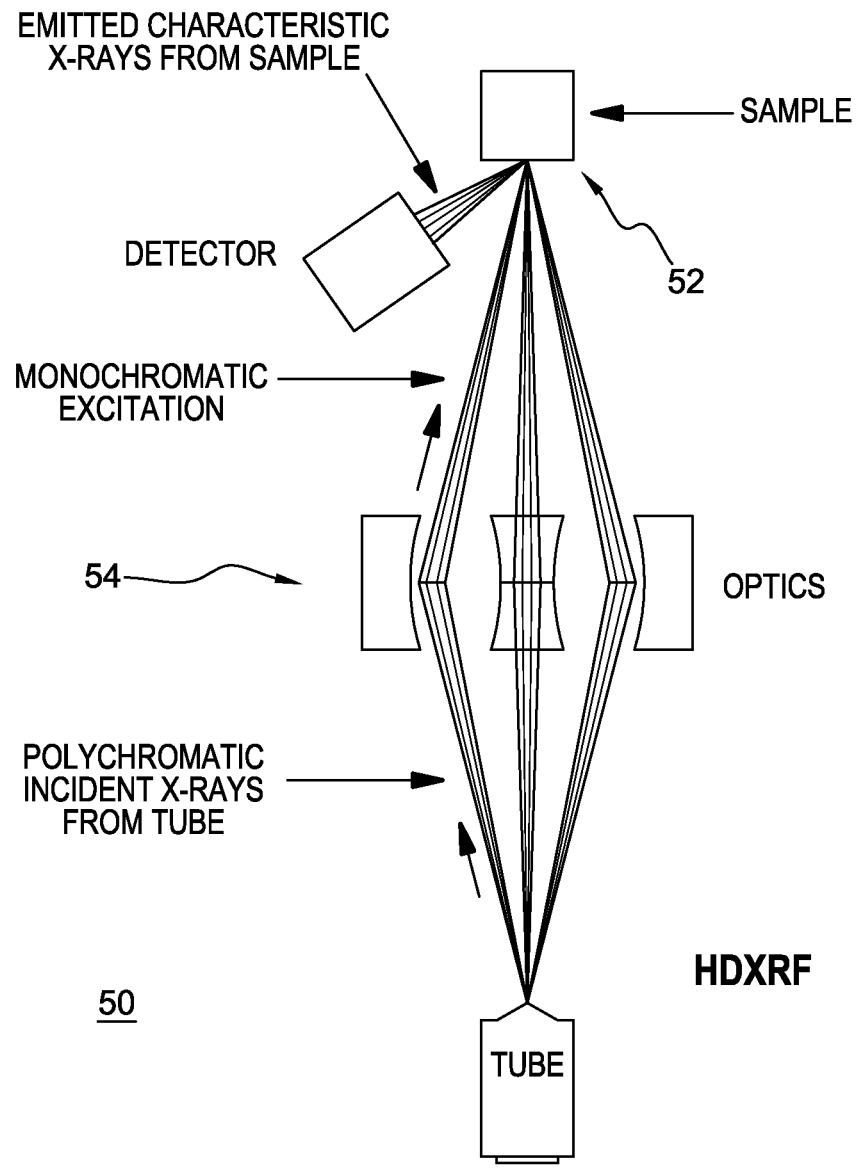
FIG. 5 is a schematic view of an exemplary ME EDXRF x-ray engine useable with the transport apparatus of the present invention.

The following are two examples of x-ray-optic-enabled analyzer engines which may be used in connection with the present invention:

Exemplary ME EDXRF X-Ray Analysis Engine:

Monochromatic excitation, energy dispersive x-ray fluorescence (ME-EDXRF) analyzers can be used for this application, in accordance with the present invention. The engine technology is disclosed in, e.g., commonly assigned US Publication 2011-0170666A1 and PCT Publication No, WO 2009111454 (A1) entitled XRF System Having Multiple Excitation Energy Bands In Highly Aligned Package, the entireties of which are hereby incorporated by reference herein. In one embodiment this engine 50 involves monochromatic excitation known as HD XRF as depicted schematically in FIG. 5. HD XRF is a multi-element analysis technique offering significantly enhanced detection performance over traditional ED or WD XRF. This technique applies state-of-the-art monochromating and focusing optics 54 illuminating a focal area 52, enabling multiple select-energy excitation beams that efficiently excite a broad range of target elements in the sample. Monochromatic excitation dramatically reduces scattering background under the fluorescence peaks, greatly enhancing elemental detection limits and precision. HDXRF is a direct measurement technique and does not require consumables or special sample preparation.

Exemplary MWD XRF X-Ray Analysis Engines:

XOS has previously disclosed a Monochromatic Wavelength Dispersive X-ray Fluorescence (MWDXRF) analyzer using two monochromating optic sets (U.S. Pat. Nos. 6,934,359 and 7,072,439—hereby incorporated by reference herein in their entirety), as shown schematically in FIG. 6. The related SINDIE (Sulfur IN DIEsel) product line for the measurement of sulfur in diesel fuel and other fuel distillates revolutionized XRF and provides many advantages including: (1) signal/background (S/B) is improved due to monochromatic excitation of the sample by DCC1, i.e., the bremsstrahlung photons with energies under fluorescence peaks (which normally swamp these peaks of interest) can only reach the detector through scattering, therefore improving the S/B ratio dramatically compared to polychromatic excitation; (2) superior energy resolution—this eliminates all common interference problems and provides the physical basis for upstream applications; (3) inherent robustness and low maintenance—the analysis engine is low power, compact, with no moving parts or consumable gasses; and (4) unprecedented dynamic range, e.g., a quantification level from 0.3 ppm to 5% of sulfur in a sample.

Figure 6:
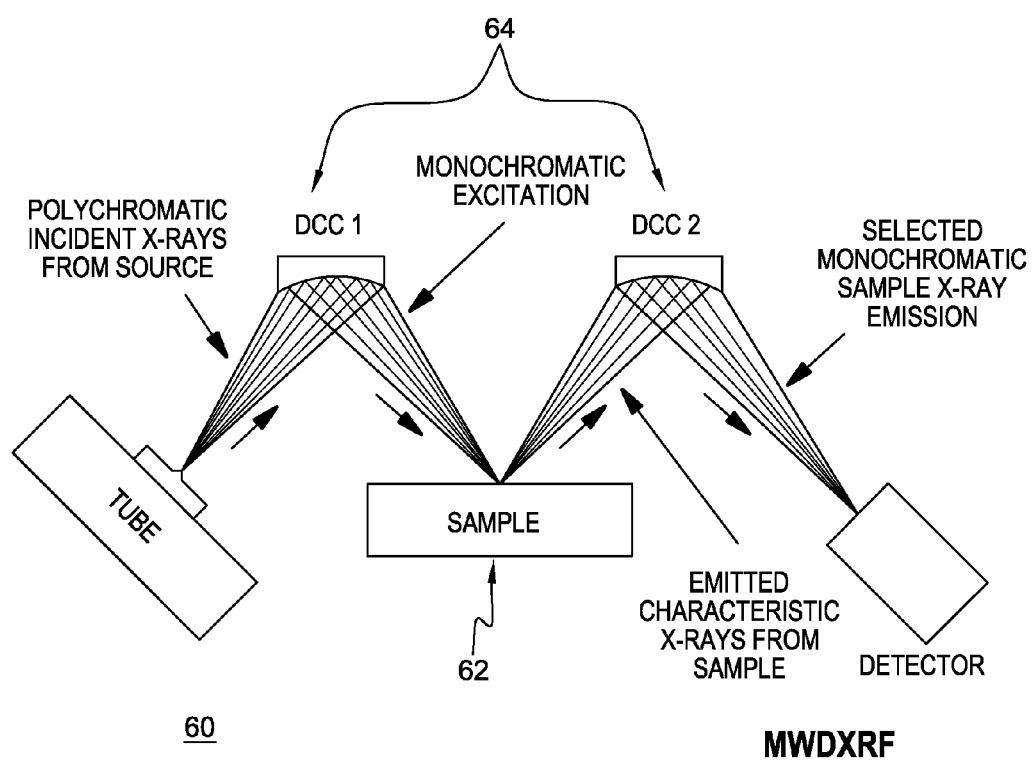
FIG. 6 a schematic view of an exemplary MWD XRF x-ray engine useable with the transport apparatus of the present invention.

The MWD XRF engine 60, shown schematically in FIG. 6, includes curved monochromating optics 64 in the excitation and detection paths, forming focal area 62, which is the configuration of the SINDIE sulfur analyzer discussed above. However, an optic may only be present in one of these paths, which still requires precise alignment. In one example, an optic of any of the above-describe types may only be present in the excitation path, and the detection path would include an energy dispersive detector. This is the common configuration of an energy dispersive x-ray fluorescence (EDXRF) system.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A mobile transport and shielding apparatus for a removable x-ray analyzer, comprising:
   an outer body forming an inner cavity;
   a sample stage in the inner cavity having a sample area for a sample;
   a cover portion of the outer body positionable around the sample area to cover and/or shield the sample area;
   means for holding the removable x-ray analyzer in the inner cavity, such that the analyzer analyzes a sample in the sample area; and
   wherein the cover portion of the outer body is interlocked to prevent x-rays from transmitting to the sample area when the cover is not positioned over the sample area.

2. A mobile transport and shielding apparatus for a removable x-ray analyzer, comprising:
   an outer body forming an inner cavity;
   a sample stage in the inner cavity having a sample area for a sample;
   a cover portion of the outer body positionable around the sample area to cover and/or shield the sample area;
   means for holding the removable x-ray analyzer in the inner cavity, such that the analyzer analyzes a sample in the sample area; and
   wherein the apparatus comprises a carrying case for the x-ray analyzer when the cover portion of the outer body is closed, using a handle on the cover portion.

3. A mobile transport and shielding apparatus for a removable x-ray analyzer, comprising:
   an outer body forming an inner cavity;
   a sample stage in the inner cavity having a sample area for a sample;
   a cover portion of the outer body positionable around the sample area to cover and/or shield the sample area;
   means for holding the removable x-ray analyzer in the inner cavity, such that the analyzer analyzes a sample in the sample area; and
   a user interface mounted on the outside of the outer body to interface to the x-ray analyzer.

4. The mobile transport and shielding apparatus of claim 3, further comprising means to control, power, cool, and/or charge the x-ray analyzer.

5. A removable x-ray analyzer in combination with a mobile transport and shielding apparatus, the mobile transport and shielding apparatus comprising:
- an outer body forming an inner cavity;
- a sample stage in the inner cavity having a sample area for a sample;
- a cover portion of the outer body positionable around the sample area to cover and/or shield the sample area;
- means for holding the removable x-ray analyzer in the inner cavity, such that the analyzer analyzes a sample in the sample area; and
- wherein the x-ray analyzer has an x-ray focal area requiring alignment with the sample in the sample area of the sample stage.

6. The combination of claim 5, further comprising at least one x-ray optic disposed in an x-ray excitation and/or detection path of the analyzer, requiring alignment to the focal area.

7. The combination of claim 6, wherein the at least one x-ray optic comprises a curved monochromating optic or a polycapillary optic.

8. A combination comprising an x-ray analyzer and a mobile transport and shielding apparatus, wherein:
- the apparatus holds the x-ray analyzer for transport between operating sites, and also serves as a shielded, operational station for holding the x-ray analyzer during operation thereof;
- the x-ray analyzer is removably insertable into the apparatus and is operable either within the mobile transport and shielding apparatus, or outside of the apparatus; and
- the apparatus comprises a user interface to interface to the x-ray analyzer.

9. The combination of claim 8, wherein the apparatus comprises means to control, power, cool, and/or charge the x-ray analyzer during operation of the analyzer.

10. A combination comprising an x-ray analyzer and a mobile transport and shielding apparatus, wherein:
- the apparatus holds the x-ray analyzer for transport between operating sites, and also serves as a shielded, operational station for holding the x-ray analyzer during operation thereof;
- the x-ray analyzer is removably insertable into the apparatus and is operable either within the mobile transport and shielding apparatus, or outside of the apparatus; and
- the x-ray analyzer comprises an x-ray focal area requiring alignment with the sample in a sample area of a sample stage of the apparatus.

11. The combination of claim 10, further comprising at least one x-ray optic disposed in an x-ray excitation and/or detection path of the x-ray analyzer, requiring alignment to the focal area.

12. The combination of claim 11, wherein the at least one x-ray optic comprises a curved monochromating optic or a polycapillary optic.

13. A combination comprising an x-ray analyzer and a mobile transport and shielding apparatus, wherein:
- the apparatus holds the x-ray analyzer for transport between operating sites, and also serves as a shielded, operational station for holding the x-ray analyzer during operation thereof;
- the x-ray analyzer is removably insertable into the apparatus and is operable either within the mobile transport and shielding apparatus, or outside of the apparatus; and
- the apparatus comprises a carrying case for the x-ray analyzer, including a handle.

* * * * *